United States Patent [19]
Chau

[11] Patent Number: 6,147,052
[45] Date of Patent: *Nov. 14, 2000

[54] METHOD OF DIFFERENTIATING ERYTHROCYTE PROGENITOR CELLS

[75] Inventor: Raymond Ming Wah Chau, Hong Kong, China

[73] Assignee: KM Biotech, Inc., Montebello, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/921,195

[22] Filed: Aug. 29, 1997

Related U.S. Application Data

[60] Provisional application No. 60/033,231, Dec. 5, 1996.

[51] Int. Cl.$^7$ .......................... C07K 14/47; A61K 38/17
[52] U.S. Cl. .......................... 514/12; 435/377; 530/324
[58] Field of Search .................... 536/23.1, 23.5; 530/350; 435/69.1, 455, 320.1; 514/12

[56] References Cited

U.S. PATENT DOCUMENTS 5,264,554  11/1993  Newman .

FOREIGN PATENT DOCUMENTS

WO9601271  1/1996  WIPO .

OTHER PUBLICATIONS

Bloom et al., J. Clin. Invest., 91:1265–1266, Apr. 1993.
D'Andrea, Alan D., Abstract as found on downloaded site from the global computer network, http://www.hms.harvard.edu/dma/virology/vir d'andrea.html, Jan. 7, 2000.
Blinder, J., "Molecular Biology of Eukaryotic Chromosomes," Madrid, Sep. 29, 1999, as found on downloaded site from the global computer network, http://www.cib.csic.es/~eucar/eucariot en.html, 3 pages, Jan. 7, 2000.
Jelinek, W., "Terminal Differentiation in Murine Erythroleukemia Cells," as found on downloaded site from the global computer network, http://www.med.nyu.edu/Research/W.Jelinek–res.html, 2 pages, Jan. 7, 2000.
Marks, P. et al., "Erythroleukemic Differentiation," *Ann. Rev. Biochem.*, 47:419–48, 1978 by Annual Reviews, Inc.
Tsiftsoglou, A.S. et al., Abstract of "Molecular and cellular mechanisms of leukemic hemopoietic cell differentiation: an analysis of the Friend system,"*Anticancer Res.*, 5(1):81–99, Jan. 1985, as found on downloaded site from the global computer network, http://www.ncbi.nlm.nih.gov/htbin-–..ery?uid=3888045&form=6&db=m&Dopt=b, Jan. 7, 2000

Biography of Tsiftsoglou, downloaded site from the global computer network, http://www.gsrt.gr/html.eng1/bioethics/memb 6.htm, Jan. 7, 2000.
Chemical Abstracts, vol. 123, No. 5, Jul. 31, 1995, Columbus, Ohio, US; abstract No. 48717, Zhang, Shi–Fu et al: "Preparation of EDDF monoclonal antibody by cell—fishing protein band and screening of its DNA Library" XP002063343, Abstract only.
Kirschbaum, N.E. et al.: "Organization of the gene for human platelet.endothelial cell adhesion molecule–1 shows alternatively spliced isoforms and functionally complex cytoplasmic domain." Blood, vol. 84, No. 12, 1994, pp. 4028–4037, XP002063338.
Chau, R.M.W. et al.: "Muscle neurotrophic factors specific for anterior horn motoneurons of rat spinal cord." Recent Advance In Cellular And Molecular Biology, vol. 5, 1991, pp. 89–94, XP002063339.
De Sauvage, F.J. et al.: "Stimulation of megakaryocytopoiesis and thrombopoiesis by the c–Mpl ligand." Nature, vol. 369, No. 1994, pp. 533–538, XP002063340.
Chan, S.S.W. et al.: "Erythroid differentiation and denucleation factors from fetal rat liver: Monoclonal antibodies preparation for clone screening from human bone marrow cDNA library." Molecular Biology Of The Cell, vol. 7, Suppl., Dec. 1996, p 533a, XP002063341, Abstract only #3100.
Chau, R.M. et al.: "Erythroid differentiation and denucleation factors from fetal rat liver: identification." Molecular Biology Of The Cell, vol. 7, Suppl., Dec. 1996, p. 519a, XP002063342, Abstract only #3021.
Ziran Zazhi (1995), 17(1), 53 Coden: TJTCD4;ISSN: 0253–9608, 1995.
English translation of Ziran Zazhi (1995), 17(1), 53 Coden: TJTCD4;ISSN: 0253–9608, 1995.

*Primary Examiner*—David Saunders
*Assistant Examiner*—Amy DeCloux
*Attorney, Agent, or Firm*—David A. Farah; Sheldon & Mak

[57] ABSTRACT

A method of differentiating erythrocyte progenitor cells comprising administering to the erythrocyte progenitor cells an effective amount of an Erythroid Differentiation and Denucleation Factor (EDDF), such that the erythrocyte progenitor cells differentiate.

4 Claims, 12 Drawing Sheets

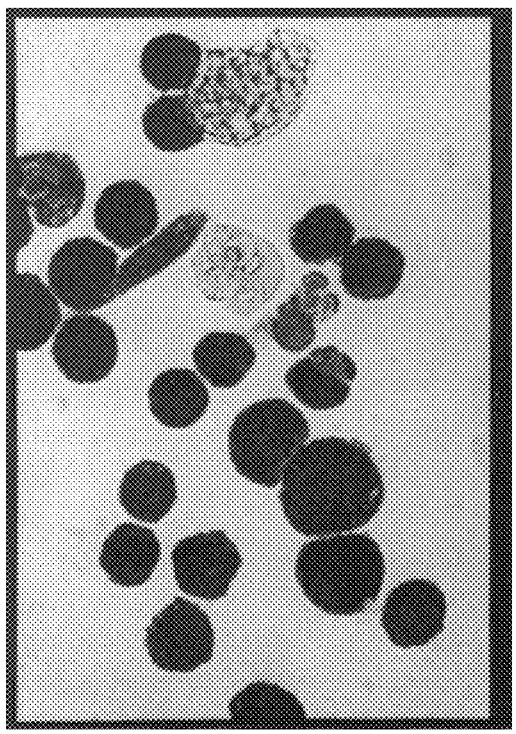 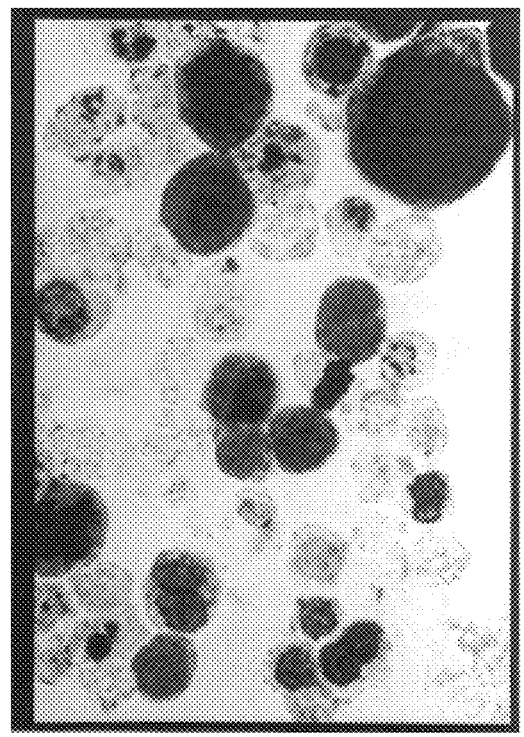
Fig. 2A-1　　　Fig. 2A-2

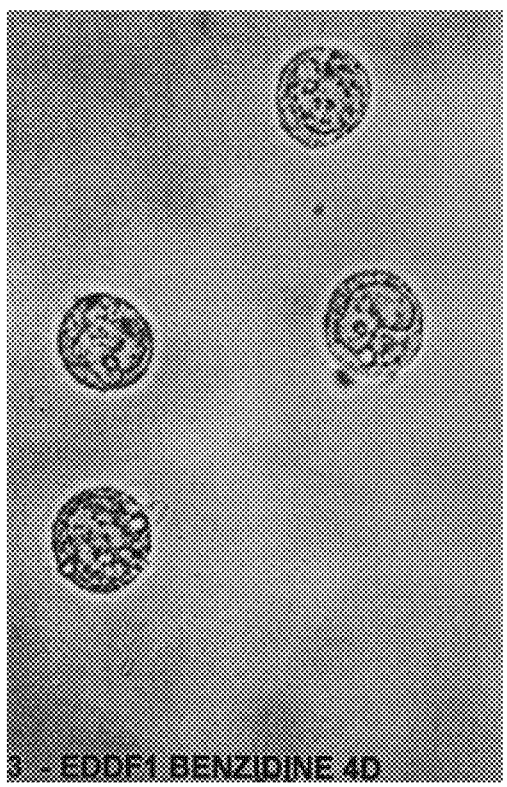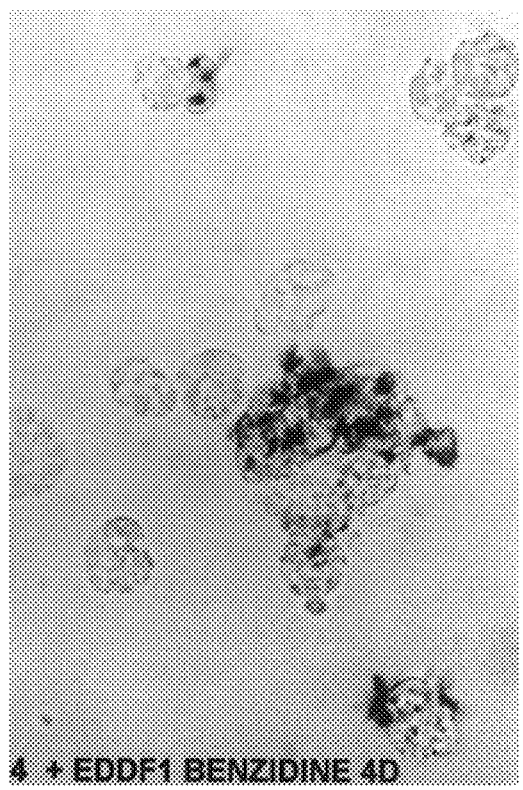
Fig. 2B-1    Fig. 2B-2

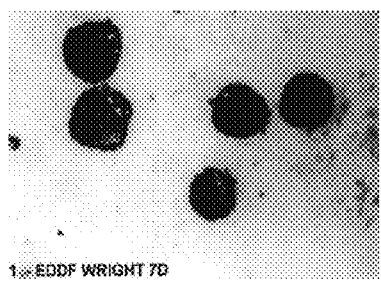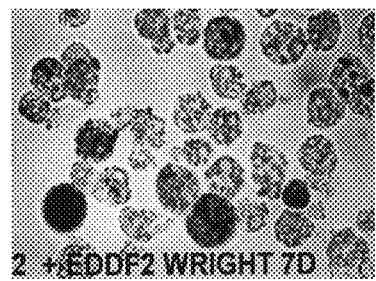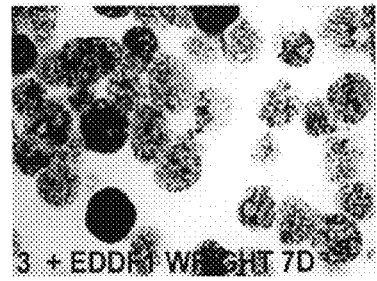
*Fig. 4B*  *Fig. 4C*  *Fig. 4D*

```
CTAATGGTGT GAGGCATACA AAAAAGAAGA CATATTCTTT GTTTCAATGC
TGTGGTAAGA AACACAAGCT CTCCTAATGA AAATGATGGA CAAACATCTG
AATCATACTA CCAATAAGCA TAGAAAAAAT GTTGGGGGTC ATGTTTGGTT
GTCACGTGAA CTATATCCTT ACAGTGATGG TGATAGTAAT TTAGGGTATG
CCAGACTTCA TCTAGCTTAA GTGGGTAAAC ATTGTGAAAA AGCTGGGCTA
GGTGCCAGGG CTTGAGAATG GGTGGCCAGA GAAGGCTGAA GATGGCTGAA
CATCTCCAGC AAACACATGA GCCAAAAGGT CCCATGGGGC ACTTCAAAAG
ACTGTGCGCA GCCAGGTGCG GTGGCTCACG CCTATAATCC CAGCACTTTG
GGAGACCGAA TGGGGTGGAT CACTTGAGCC CAGAGGTTTG TGACTAGCTT
GGCCAACATG GCAAAACCCC GTCTCTACTA AAAATACAAA AATTAGCCCA
GCGTGGTGGT GGGTGTCCTG TAGCCCCAGC TACTCAGGTG GCTGAGGTGG
TAGAATCACT TGAATCCAGG AGGCAGAGGT TGCAGTGAGC CAAGATCGTG
CCACTGCACT CCAGCCTGGG TGACAGAGTG AGACTCTATC TCCACAAAAA
AAAAAAAAAA AAAAAAATT AAAGGACTGT GGCCAAATCA GATGGCTGGA
AACAAAGGCT GGAGTTTGGG AATGGAGAAT CACCGGATAT GAGCTGAAAA
AGTGGCTGAG CCTAAGCGTG ACAGGTGTCA GGTGCCAGTC TCAGGAGTAG
GCAAGTGTCC TGCATGCAGT GAAAAGCCAG AAGATGGAAG GAAGAACAGG
ATGCAAATGA GTTCTCGGAA CGATCCACCT GGTGGCTGGG TCAGGGAGCA
GGCATGGTGA CTTCAGACCT CATGGTACGT TAGAGGCTAA TGTGAAGCCC
ATGTGAAGCT GTTGGTTTAA ACTGGGTCGA TATCAGTGGC ACACATTTAC
TGACCATGTG TCCAGCCCTG TGTGAAGTAC TGTAGTAAAT TGCTCCAATG
GAAACTCACA ATAACCACAG AAGGCCAGTA ACAGCATTGT CGTTATTTTA
TCATGACGCA ACTGAGGCTT AGGGCAGACA GCTGGTGGGT GGTGGGACTG
GGATTTGAGC CCACTGGTGT CCCAGGCCCG GAGCTTGGCT TCTTCCATTG
TCTTACCACA GCCTGCACTC ACAGGAGAGT GACCTATAAG TTACAATACC
ATCTGCTGAC CATCTGCTCT CACACTAGAA GGAAAGTCTA CTTGGGGAGA
CAATTTAGGA TCCGAATTTT GGTAGTTGAG GATGGAGCTA GGAAAAGCGG
ATACAGGAGG TAGCCAAGTT CTGCTTGGAC CTGCAGGGAG TGAGGCTGGC
CGGGCTCCAG GTGGAAATCC CCAGGTGAAA AGGGAGACTT GGAGGTCAGG
AAAGTAACCT GGACTGGAGC CATAGGTTTA GGTGTCAGTG GCTCAGAGAC
AGAAGCTCAG CGTGTAGGTG AAATCACCCA GGAGGAGAAT GGGGATGGAA
AACTGAGGAT TGAATTTTGC AAAATGTTCA TACTTCCGGG AAAACAAAG
AATAACCAGT GAATAAGAAA GGGGTGCCAG GTAAGAAGGG AAGAGAATCA
GAGTCATGAG GAACCCCAGA ACCCCAGAAA AGCTGAGTT CCACGTAAGA
CCTGGGCAAC AGTGAAGTAT GGAGAGCCCA AGATTGGGAG CGTGGAGGAA
GAGCATCCAC CACTGAATTT AATCAGCCCC GGACTCAGGG ACGTTGGTTG
GGGAATCAAG TGACCTTCCC AGTTTCTTCA AAACTTGAGA GAGAGTGCAG
TGTCACAAGA TTGTGACTAC AAAAGAGTGC AGTCAGATTT CAGGGGTAAC
AAGAAAGTGT GAAATAAGGG AGTCAAAGCA TAAAGGAAAA AGGAGAAAAA
ATGGCCGATA GCTAGAGAAG GCGTGGGTCA AGATTGTCTG TGGCCTGGCA
TGGTGGCTTA TGCCTGTAAT CCCAGCATTT TGGAAGGCCG AGGTGGGCAA
ATCACCTGAG GTCAGGAATT CAAGACCAGC CTGGCCAACA GGGCAAAACC
CCGTCTCTAA AACAACAACA ACAACAAAAA AATCCAAAAA GTTAGCTGGG
CCTGGTGGGC GCACCTGTCA TTCCAGCTAC TCGGGAGGCT GAGGCAGGAG
ATTTGCTTGA ACCCAGGAGG CACACGTTGC GGTAAGCTGA GATTATACCA
CTGCACTCCA GCCTGGGTGA TAAGAGCGGG ACTCTGTCTC AGAGGAAAAA
AAAAAAAGTT GAGCAGTGGC TGTCTCATGT TCCTCTTCCT CTGCCCTTCT
TTGCTCAGTG TGAATCCTTT TCCTGCTTTT CAGCCCCGGT GGATGAGGTC
CAGATTTCTA TCCTGTCAAG TAAGGTGGTG GAGTCTGGAG AGGACATTGT
GCTGCAATGT GCTGTGAATG AAGGATCTGG TCCCATCACC TATAAGTTTT
```

*Figure 8A-1*

```
ACAGAGAAAA AGAGGGCAAA CCCTTCTATC AAATGACCTC AAATGCCACC
CAGGCATTTT GGACCAAGCA GAAGGCTAAC AAGGAACAGG AGGGAGAGTA
TTACTGCACA GCCTTCAACA GAGCCAACCA CGCCTCCAGT GTCCCCAGAA
GCAAAATACT GACAGTCAGA GGTGAGTCAG GGTCTCCATA GCAAGCTGTG
CTGTGGGCCC CCAAGGGCAA G
```

Figure 8A-2

```
                    GAATT CAAGACCAGC CTGGCCAACA GGGCAAAACC
CCGTCTCTAA AACAACAACA ACAACAAAAA AATCCAAAAA GTTAGCTGGG
CCTGGTGGGC GCACCTGTCA TTCCAGCTAC TCGGGAGGCT GAGGCAGGAG
ATTTGCTTGA ACCCAGGAGG CACACGTTGC GGTAAGCTGA GATTATACCA
CTGCACTCCA GCCTGGGTGA TAAGAGCGGG ACTCTGTCTC AGAGGAAAAA
AAAAAAAGTT GAGCAGTGGC TGTCTCATGT TCCTCTTCCT CTGCCCTTCT
TTGCTCAGTG TGAATCCTTT TCCTGCTTTT CAGCCCCGGT GGATGAGGTC
CAGATTTCTA TCCTGTCAAG TAAGGTGGTG GAGTCTGGAG AGGACATTGT
GCTGCAATGT GCTGTGAATG AAGGATCTGG TCCCATCACC TATAAGTTTT
ACAGAGAAAA AGAGGGCAAA CCCTTCTATC AAATGACCTC AAATGCCACC
CAGGCATTTT GGACCAAGCA GAAGGCTAAC AAGGAACAGG AGGGAGAGTA
TTACTGCACA GCCTTCAACA GAGCCAACCA CGCCTCCAGT GTCCCCAGAA
GCAAATACT GACAGTCAGA GGTGAGTCAG GGTCTCCATA GCAAGCTGTG
CTGTGGGCCC CCAAGGGCAA G
```

Figure 8B

```
                              GCCCCGGT GGATGAGGTC
CAGATTTCTA TCCTGTCAAG TAAGGTGGTG GAGTCTGGAG AGGACATTGT
GCTGCAATGT GCTGTGAATG AAGGATCTGG TCCCATCACC TATAAGTTTT
ACAGAGAAAA AGAGGGCAAA CCCTTCTATC AAATGACCTC AAATGCCACC
CAGGCATTTT GGACCAAGCA GAAGGCTAAC AAGGAACAGG AGGGAGAGTA
TTACTGCACA GCCTTCAACA GAGCCAACCA CGCCTCCAGT GTCCCCAGAA
GCAAATACT GACAGTCAGA
```

Figure 9

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2721 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| CTAATGGTGT | GAGGCATACA | AAAAAGAAGA | CATATTCTTT | GTTTCAATGC | TGTGGTAAGA | 60 |
| AACACAAGCT | CTCCTAATGA | AAATGATGGA | CAAACATCTG | AATCATACTA | CCAATAAGCA | 120 |
| TAGAAAAAAT | GTTGGGGGTC | ATGTTTGGTT | GTCACGTGAA | CTATATCCTT | ACAGTGATGG | 180 |
| TGATAGTAAT | TTAGGGTATG | CCAGACTTCA | TCTAGCTTAA | GTGGGTAAAC | ATTGTGAAAA | 240 |
| AGCTGGGCTA | GGTGCCAGGG | CTTGAGAATG | GGTGGCCAGA | GAAGGCTGAA | GATGGCTGAA | 300 |
| CATCTCCAGC | AAACACATGA | GCCAAAAGGT | CCCATGGGGC | ACTTCAAAAG | ACTGTGCGCA | 360 |
| GCCAGGTGCG | GTGGCTCACG | CCTATAATCC | CAGCACTTTG | GGAGACCGAA | TGGGGTGGAT | 420 |
| CACTTGAGCC | CAGAGGTTTG | TGACTAGCTT | GGCCAACATG | GCAAAACCCC | GTCTCTACTA | 480 |
| AAAATACAAA | AATTAGCCCA | GCGTGGTGGT | GGGTGTCCTG | TAGCCCCAGC | TACTCAGGTG | 540 |
| GCTGAGGTGG | TAGAATCACT | TGAATCCAGG | AGGCAGAGGT | TGCAGTGAGC | CAAGATCGTG | 600 |
| CCACTGCACT | CCAGCCTGGG | TGACAGAGTG | AGACTCTATC | TCCACAAAAA | AAAAAAAAAA | 660 |
| AAAAAAATT | AAAGGACTGT | GGCCAAATCA | GATGGCTGGA | AACAAAGGCT | GGAGTTTGGG | 720 |
| AATGGAGAAT | CACCGGATAT | GAGCTGAAAA | AGTGGCTGAG | CCTAAGCGTG | ACAGGTGTCA | 780 |
| GGTGCCAGTC | TCAGGAGTAG | GCAAGTGTCC | TGCATGCAGT | GAAAAGCCAG | AAGATGGAAG | 840 |
| GAAGAACAGG | ATGCAAATGA | GTTCTCGGAA | CGATCCACCT | GGTGGCTGGG | TCAGGGAGCA | 900 |
| GGCATGGTGA | CTTCAGACCT | CATGGTACGT | TAGAGGCTAA | TGTGAAGCCC | ATGTGAAGCT | 960 |
| GTTGGTTTAA | ACTGGGTCGA | TATCAGTGGC | ACACATTTAC | TGACCATGTG | TCCAGCCCTG | 1020 |
| TGTGAAGTAC | TGTAGTAAAT | TGCTCCAATG | GAAACTCACA | ATAACCACAG | AAGGCCAGTA | 1080 |
| ACAGCATTGT | CGTTATTTTA | TCATGACGCA | ACTGAGGCTT | AGGGCAGACA | GCTGGTGGGT | 1140 |
| GGTGGGACTG | GGATTTGAGC | CCACTGGTGT | CCCAGGCCCG | GAGCTTGGCT | TCTTCCATTG | 1200 |
| TCTTACCACA | GCCTGCACTC | ACAGGAGAGT | GACCTATAAG | TTACAATACC | ATCTGCTGAC | 1260 |
| CATCTGCTCT | CACACTAGAA | GGAAAGTCTA | CTTGGGGAGA | CAATTTAGGA | TCCGAATTTT | 1320 |
| GGTAGTTGAG | GATGGAGCTA | GGAAAAGCGG | ATACAGGAGG | TAGCCAAGTT | CTGCTTGGAC | 1380 |
| CTGCAGGGAG | TGAGGCTGGC | CGGGCTCCAG | GTGGAAATCC | CCAGGTGAAA | AGGGAGACTT | 1440 |
| GGAGGTCAGG | AAAGTAACCT | GGACTGGAGC | CATAGGTTTA | GGTGTCAGTG | GCTCAGAGAC | 1500 |
| AGAAGCTCAG | CGTGTAGGTG | AAATCACCCA | GGAGGAGAAT | GGGGATGGAA | AACTGAGGAT | 1560 |
| TGAATTTTGC | AAAATGTTCA | TACTTCCGGG | GAAAACAAAG | AATAACCAGT | GAATAAGAAA | 1620 |
| GGGGTGCCAG | GTAAGAAGGG | AAGAGAATCA | GAGTCATGAG | GAACCCCAGA | ACCCCAGAAA | 1680 |
| AAGCTGAGTT | CCACGTAAGA | CCTGGGCAAC | AGTGAAGTAT | GGAGAGCCCA | AGATTGGGAG | 1740 |
| CGTGGAGGAA | GAGCATCCAC | CACTGAATTT | AATCAGCCCC | GGACTCAGGG | ACGTTGGTTG | 1800 |
| GGGAATCAAG | TGACCTTCCC | AGTTTCTTCA | AAACTTGAGA | GAGAGTGCAG | TGTCACAAGA | 1860 |
| TTGTGACTAC | AAAAGAGTGC | AGTCAGATTT | CAGGGGTAAC | AAGAAAGTGT | GAAATAAGGG | 1920 |
| AGTCAAAGCA | TAAAGGAAAA | AGGAGAAAAA | ATGGCCGATA | GCTAGAGAAG | GCGTGGGTCA | 1980 |
| AGATTGTCTG | TGGCCTGGCA | TGGTGGCTTA | TGCCTGTAAT | CCCAGCATTT | TGGAAGGCCG | 2040 |
| AGGTGGGCAA | ATCACCTGAG | GTCAGGAATT | CAAGACCAGC | CTGGCCAACA | GGGCAAAACC | 2100 |
| CCGTCTCTAA | AACAACAACA | ACAACAAAAA | AATCCAAAAA | GTTAGCTGGG | CCTGGTGGGC | 2160 |
| GCACCTGTCA | TTCCAGCTAC | TCGGGAGGCT | GAGGCAGGAG | ATTTGCTTGA | ACCCAGGAGG | 2220 |
| CACACGTTGC | GGTAAGCTGA | GATTATACCA | CTGCACTCCA | GCCTGGGTGA | TAAGAGCGGG | 2280 |

```
ACTCTGTCTC AGAGGAAAAA AAAAAAAGTT GAGCAGTGGC TGTCTCATGT TCCTCTTCCT    2340

CTGCCCTTCT TTGCTCAGTG TGAATCCTTT TCCTGCTTTT CAGCCCCGGT GGATGAGGTC    2400

CAGATTTCTA TCCTGTCAAG TAAGGTGGTG GAGTCTGGAG AGGACATTGT GCTGCAATGT    2460

GCTGTGAATG AAGGATCTGG TCCCATCACC TATAAGTTTT ACAGAGAAAA AGAGGGCAAA    2520

CCCTTCTATC AAATGACCTC AAATGCCACC CAGGCATTTT GGACCAAGCA GAAGGCTAAC    2580

AAGGAACAGG AGGGAGAGTA TTACTGCACA GCCTTCAACA GAGCCAACCA CGCCTCCAGT    2640

GTCCCCAGAA GCAAAATACT GACAGTCAGA GGTGAGTCAG GGTCTCCATA GCAAGCTGTG    2700

CTGTGGGCCC CCAAGGGCAA G                                               2721

(2) INFORMATION FOR SEQ ID NO:2:

(i) SEQUENCE CHARACTERISTICS:
        (A) LENGTH: 656 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GAATTCAAGA CCAGCCTGGC CAACAGGGCA AAACCCCGTC TCTAAAACAA CAACAACAAC      60

AAAAAAATCC AAAAAGTTAG CTGGGCCTGG TGGGCGCACC TGTCATTCCA GCTACTCGGG     120

AGGCTGAGGC AGGAGATTTG CTTGAACCCA GGAGGCACAC GTTGCGGTAA GCTGAGATTA     180

TACCACTGCA CTCCAGCCTG GGTGATAAGA GCGGGACTCT GTCTCAGAGG AAAAAAAAAA     240

AAGTTGAGCA GTGGCTGTCT CATGTTCCTC TTCCTCTGCC CTTCTTTGCT CAGTGTGAAT     300

CCTTTTCCTG CTTTTCAGCC CCGGTGGATG AGGTCCAGAT TTCTATCCTG TCAAGTAAGG     360

TGGTGGAGTC TGGAGAGGAC ATTGTGCTGC AATGTGCTGT GAATGAAGGA TCTGGTCCCA     420

TCACCTATAA GTTTTACAGA GAAAAGAGG GCAAACCCTT CTATCAAATG ACCTCAAATG     480

CCACCCAGGC ATTTTGGACC AAGCAGAAGG CTAACAAGGA ACAGGAGGGA GAGTATTACT     540

GCACAGCCTT CAACAGAGCC AACCACGCCT CCAGTGTCCC CAGAAGCAAA ATACTGACAG     600

TCAGAGGTGA GTCAGGGTCT CCATAGCAAG CTGTGCTGTG GGCCCCCAAG GGCAAG         656

(2) INFORMATION FOR SEQ ID NO:3:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCCCCGGTGG ATGAGGTCCA GATTTCTATC CTGTCAAGTA AGGTGGTGGA GTCTGGAGAG      60

GACATTGTGC TGCAATGTGC TGTGAATGAA GGATCTGGTC CCATCACCTA TAAGTTTTAC     120

AGAGAAAAAG AGGGCAAACC CTTCTATCAA ATGACCTCAA ATGCCACCCA GGCATTTTGG     180

ACCAAGCAGA AGGCTAACAA GGAACAGGAG GGAGAGTATT ACTGCACAGC CTTCAACAGA     240

GCCAACCACG CCTCCAGTGT CCCCAGAAGC AAAATACTGA CAGTCAGA                  288

(2) INFORMATION FOR SEQ ID NO:4:

(i) SEQUENCE CHARACTERISTICS:
```

-continued

```
    (A) LENGTH: 96 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

Ala Pro Val Asp Glu Val Gln Ile Ser Ile Leu Ser Ser Lys Val Val
1               5                   10                  15

Glu Ser Gly Glu Asp Ile Val Leu Gln Cys Ala Val Asn Glu Gly Ser
            20                  25                  30

Gly Pro Ile Thr Tyr Lys Phe Tyr Arg Glu Lys Glu Gly Lys Pro Phe
            35                  40                  45

Tyr Gln Met Thr Ser Asn Ala Thr Gln Ala Phe Trp Thr Lys Gln Lys
    50                  55                  60

Ala Asn Lys Glu Gln Glu Gly Glu Tyr Tyr Cys Thr Ala Phe Asn Arg
65                  70                  75                  80

Ala Asn His Ala Ser Ser Val Pro Arg Ser Lys Ile Leu Thr Val Arg
                85                  90                  95
```

METHOD OF DIFFERENTIATING ERYTHROCYTE PROGENITOR CELLS

RELATED APPLICATIONS

This Patent application is a continuation in part of Provisional Patent Application U.S. Ser. No. 60/033,231, filed on Dec. 5, 1996, which is hereby incorporated by reference.

FIELD OF INVENTION

The present invention relates to human genes which encode a specialized group of proteins which function to promote the growth, differentiation, and denucleation of immature erythrocytes (red blood cells) and erythroid leukemic cells.

BACKGROUND OF INVENTION

During erythropoiesis, red blood cells are matured in fetal liver or adult bone marrow through the proliferation and differentiation of committed progenitor cells, which are the erythroid burst forming unit and the erythroid-colony forming unit. These progenitor cells are dependent upon lineage-specific growth factors for their proliferation and differentiation. In contrast, primitive pluripotent hematopoietic stem cells, which are generally quiescent and are triggered to proliferate only when a need is expressed in the periphery, respond to a combination of multiple hematopoietic growth factors. Recently, several factors have been identified that appear to be involved in the triggering of cell division in the quiescent hematopoietic progenitor cells and in the differentiation of committed progenitor cells. It has been demonstrated that burst promoting factor (BPF), colony stimulating factor (CSF), and interleukin-3 (IL-3) have a dependent-effect upon the proliferation and differentiation of pluripotent stem cells and progenitor cells. Additional studies have also determined that erythropoietin (EPO) is the sole factor involved in the late stages of erythroid differentiation prior to the stage of basophilic erythroblast. However, the role of these factors in the regulation of the final differentiation stages, beyond basophilic eythroblast, are still uncertain.

Numerous types of cells express cell-surface proteins known as "integrins" which are recognized by extracellular proteins such as fibronectin, collagen, osteoprotein, fibrinogen, vitronectin, thrombospondin, and Von Willebrand factor (VWF), which function in the attachment of these cells to their surroundings. Integrins, which act as receptors for several of these aforementioned extracellular proteins, have been identified with human platelet glycoprotein—which functions to mediate VWF-dependent adhesion of platelets to exposed vascular endothelium.

Another common group of adhesion-promoting molecules are referred to generically as "cellular adhesion molecules" (CAMs) which are glycosylated proteins belonging to the immunoglobulin super-family. The classified CAMs include: neuronal cellular adhesion molecule (NCAM); myelin-associated glycoprotein (MAG); intercellular adhesion molecule (ICAM); lymphocyte function-associated antigen-3 (LFA-3); the T-cell subset cell-surface marker CD-4; the major glycoprotein of peripheral myelin (Po); carcinoembryonic antigen (CEA); and platelet-endothelial cell adhesion molecule 1 (PECAM-1). See e.g., Williams, D. F. & Barclay, T., 6 *Ann. Rev. Immunol.* 381 (1988).

Of particular interest in the instant invention, is platelet-endothelial cell adhesion molecule 1 (PECAM-1). These cellular adhesion molecules typically are comprised of 711 amino acids and possess a molecular weight of 130 kd. PECAM-1 has been demonstrated to be expressed on platelets, circulating monocytes, and at the intercellular junctions of resting endothelial cells. See e.g., Ashman & Aylett, 38 *Tissue Antigen* 208 (1991). PECAM-1's are important mediators of platelet-platelet, platelet-leukocyte, and platelet-endothelial cell interactions in the process of platelet aggregation. In addition, these molecules may also be involved in the development of atherosclerotic plaque and thrombi from vascular trauma (e.g., from angioplasty), as well as in leukocyte-endothelial cell interactions in inflammation and transendothelial cell migration.

DESCRIPTION OF THE FIGURES

The present invention may be better-understood and its advantages appreciated by those individuals skilled in the relevant art by referring to the accompanying figures wherein:

FIG. 2A—Illustrates the morphological characteristics of murine erythroid leukemia (MEL) cells co-cultured with fetal rat liver extract by use of Wright stain. 2B—Illustrates benzidine reaction measurements for -globin.

FIG. 4 FIG. 4A illustrates the percentage of murine erythroid leukemia, as determined by a differential cell count (FIGS. 4B–4D), of (MEL) cells following a 7-day co-culture with various electrophoretically-separated protein bands from fetal rat liver extract.

FIG. 8 8A—DNA sequence of the large, 2721 bp EDDF1 EcoRl-generated cDNA fragment, SEQ ID NO: 1 derived from the human bone marrow cDNA library. 8B—depicts the DNA sequence of the smaller, 650 bp EcoRl-generated cDNA fragment, SEQ ID NO: 2. 8C—depicts the DNA sequence of the 288 bp EcoRl-generated, translatable hrEDDF1, SEQ ID NO: 3. By standard convention the DNA sequence is shown in the 5' to 3' orientation.

FIG. 9 depicts the amino acid sequence, SEQ ID NO:4, encoded by the 288 bp. EcoRl-generated, translatable hrEDDF1. By standard convention the amino acid sequence is shown from the —$NH_2$ to —COOH terminus.

SUMMARY OF THE INVENTION

Figure 1:
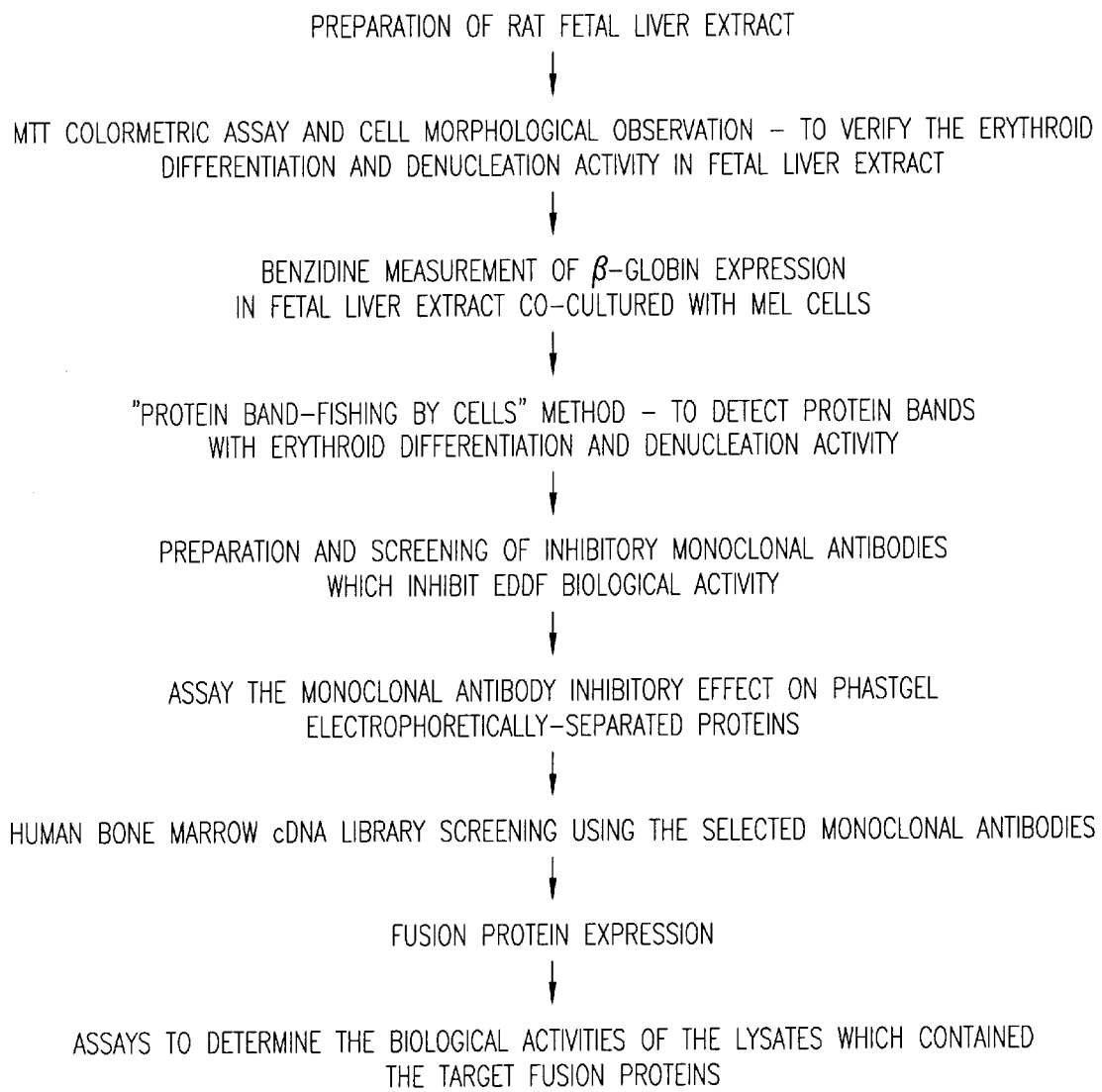
FIG. 1 Illustrates a flow-chart of the various experimental methodologies utilized in these series of experiments.

The present invention is directed to a family of erythroid differentiation and denucleation factors (EDDFs) including EDDF1 (17 kDa) and EDDF2 (94 kDa), which have been shown to possess diagnostic and therapeutic applicability in mammals.

The present invention is also directed to a novel genomic DNA sequence which encodes human EDDF1, a vector which contains this novel DNA sequence, an expression system and associated transformed host which contains the novel DNA sequence, and which is also capable of expressing the novel recombinant human EDDF1 protein.

DETAILED DESCRIPTION OF THE INVENTION

The present invention utilizes a methodology named "Protein Band-Fishing by Cells" (see Chau, R. M. W., et al., Muscle Neuronotrophic Factors Specific for Anterior Horn Motoneurons of Rat Spinal Cord. In: *Recent Advances in Cellular and Molecular Biology*, Vol. 5, Peeters Press, Leuven, Belgium, pp. 89–94 (1992)) in an attempt to identify various erythroid differentiation and denucleation factors (EDDFs).

The novel methodology of "Protein Band-Fishing by Cells" was applied to identify the erythroid differentiation and denucleation factor (EDDF) activities in fetal rat liver extract on the growth and differentiation of murine erythroid leukemia (MEL) cells in vitro. See Chan, S. S. W., et al., *Erythroid Differentiation and Denucleation Factors from Fetal Rat Liver: Monoclonal Antibodies Preparation for Clone Screening from Human Bone Marrow cDNA Library*, (Abstract), 6th International Congress on Cell Biology (1996); Chau, R. M. W. et al., *Effects of the Rat Fetal Liver Extract on the Proliferation and Differentiation of Murine Erythroid Leukemia Cells*, (Abstract), 6th International Congress on Cell Biology (1996), whose disclosures are incorporated herein by reference. As the fetal liver has been shown to be one of the progenitors of fetal blood stem cells (which contain factors for erythroid differentiation) prior to the development of the bone marrow, fetal liver extract, obtained from embryonic-15-day Sprague Dawley rat fetus, was used as the source of EDDF in an attempt to identify and isolate specific EDDF(s) in vitro. Proteins present in the fetal rat liver extract were electrophoretically-separated in native form utilizing the PHASTGEL electrophoresis system (LKB Pharmacia).

After isolation of protein bands, monoclonal antibodies were made to the proteins and screened for their ability to inhibit the differentiation and denucleation activities of the isolated proteins. These antibodies were then used to immunoselect clones containing genes coding for the desired functions.

The inserts from the selected clones were isolated and their DNA was sequenced. Some sequences were subdloned to obtain the most efficient clones of the EDDF genes. The subdlones were tested for expression of proteins with the appropriate biological activity. The amino acid sequence of the protein was then determined. It was discovered that there was homology between the isolated EDDF protein and one exon of an unrelated cell adhesion protein, PECAM. However, the subcloned sequence which expressed this EDDF is somewhat shorter than the PECAM sequence disclosed.

A flow-chart of the various methodologies utilized in the following series of experiments is illustrated in FIG. 1.

EXAMPLE 1

Co-Culture of Murine Erythroid Leukemia Cells with Fetal Rat Liver Extract

Murine erythroid leukemia (MEL) cells were co-cultured with fetal rat liver extract (FRLE) at a concentration of 0.4 mg/ml. FIG. 2A depicts the morphological characteristics of the MEL cells co-cultured with the FRLE and illustrates a basophilic staining of the MEL cell cytoplasm after day 4. Generally, it was found that the nuclei of the MEL cells became smaller, more compact, and more intensely stained as a function of their total time in culture. The total number of MEL cells without a nucleus (reticulocytes) gradually increased from 5.4% on day 2 to 56% on day 7.

FIG. 2B, panel b illustrates the results of measurement of benzidine (a substrate for the peroxidase activity B-globin). Measurable enzymatic reaction (as shown by the accumulation of dark-greenish granules in the cytoplasm) was only found in the cytoplasm of MEL cells co-cultured with FRLE.

Similarly, MEL cells were co-cultured with FRLE at concentrations of 0.1, 0.2, and 0.4 mg/ml. 1.8% dimethyl sulfoxide (DMSO), a differentiation inducer, was utilized as a negative control for cell growth, whereas DMEM medium was utilized as a positive control. The determination of MEL cell viability and the influence of the FRLE on MEL cell growth was performed utilizing both MTT microassay wherein the optical density of the cell culture was determined at 570–630 nm and morphological measurement via inverted phase microscopy (Zeiss Axiophot Inverted Microscope, West Germany). MTT is a tetrazolium derivative [3-(4,5-dimethylthiazol-2-yl)-2,5-dipheny tetrazolium bromide] which can be converted by viable cells to form a formazan product which can subsequently be measured with an ELISA colorimeter.

Figure 3:
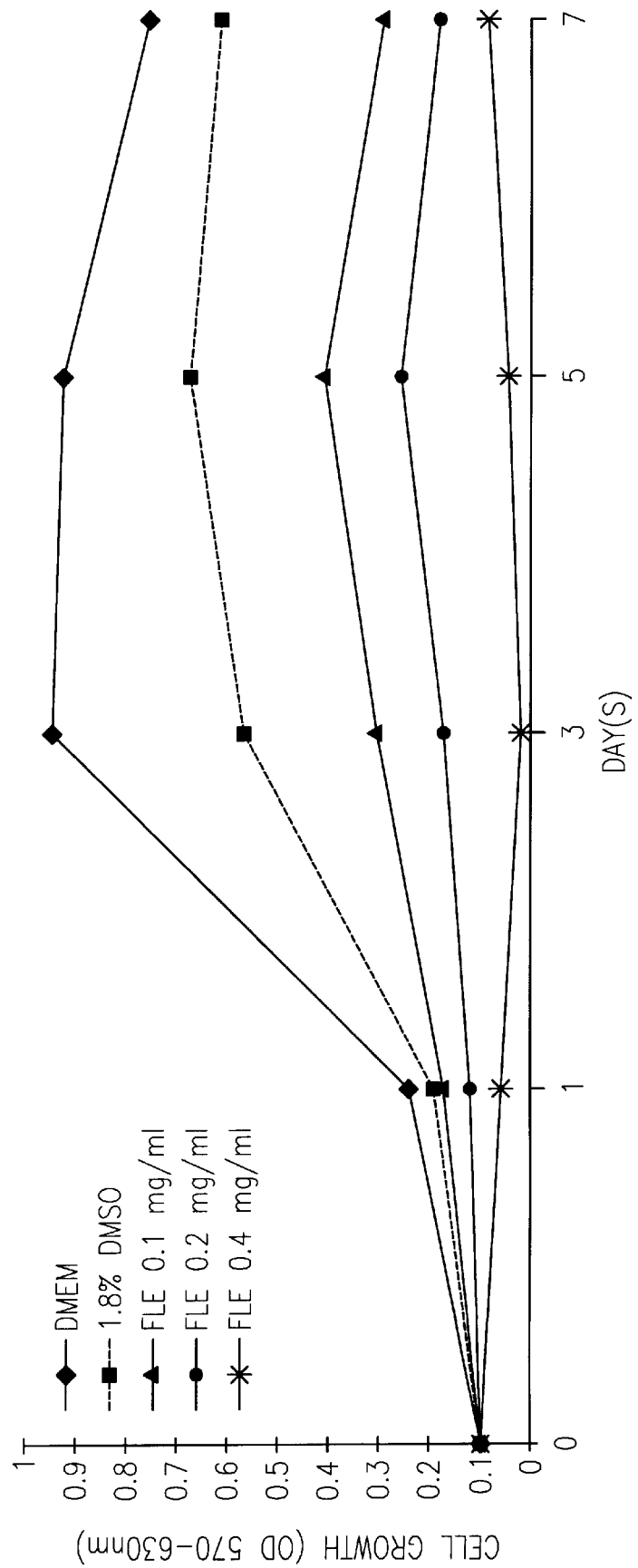
FIG. 3 Illustrates the influence, as determined by an MTT microcolormetric assay, of varying concentration of fetal rat liver extract on the growth and differentiation of murine erythroid leukemia (MEL) cells in vitro.

The results of the MTT colormetric assays, illustrated in FIG. 3, demonstrated that greater concentrations of FRLE caused increased inhibition of MEL cell growth. For example, with a 0.2 mg/ml FRLE concentration, a 5.5-fold inhibition of MEL cell growth was observed on day 3 when compared with the negative control (cells cultured with DMEM medium alone). It was found that the higher the concentration of FRLE, the greater the inhibition of MEL cell growth in culture.

EXAMPLE 2

Isolation of EDDFs by the "Protein Band-Fishing by Cells" Methodology

The erythroid differentiation and denucleation factor (EDDF) in fetal rat liver extract (FRLE) was isolated utilizing the proprietary "Protein Band-Fishing by Cells" methodology as initially reported in Chau, R. M. W., et al., Muscle Neuronotrophic Factors Specific for Anterior Horn Motoneurons of Rat Spinal Cord. In: *Recent Advances in Cellular and Molecular Biology*, Vol. 5, Peeters Press, Leuven, Belgium, pp. 89–94 (1992). Additionally, this methodology allowed for the determination of the effect of EDDF on the growth and differentiation of murine erythroid leukemia (MEL) cells in vitro. See Chan, S. S. W., et al., *Erythroid Differentiation and Denucleation Factors from Fetal Rat Liver: Monoclonal Antibodies Preparation for Clone Screening from Human Bone Marrow cDNA Library*, (Abstract), 6th International Congress on Cell Biology (1996); Chau, R. M. W. et al., *Effects of the Rat Fetal Liver Extract on the Proliferation and Differentiation of Murine Erythroid Leukemia Cells*, (Abstract), 6th International Congress on Cell Biology (1996).

Erythroid differentiation and denucleation factors are generally found in minute quantities in vivo this can potentially cause tremendous difficulties in their isolation utilizing traditional biochemical methodologies. In view of this fact, a novel technique designated "Protein Band-Fishing by Cells" was developed in which viable MEL cells were co-cultured with an electrophoretic gel containing the separated proteins from fetal rat liver extract (FRLE). This methodology thus allowed the MEL cells to "fish-out" those fetal rat liver extract proteins which exhibited biological activity specific for those erythroid leukemic cells (i.e., differentiation and denucleation of MEL cells into reticulocytes or mature erythrocytes).

For electrophoretic protein separation, the livers from embryonic 15 day-old Sprague Dawley rats fetuses were aseptically dissected into small sections and washed 3-times in $Ca^{+2}/Mg^{+2}$-free Hank's medium. The hepatic tissue was then homogenized in 10 mM Tris-HCl (pH 7.2). A cell lysate was obtained by centrifugation at 3,000 r.p.m. for 10 minutes, and the supernatant was filtered utilizing a 0.2 μm Millipore filter membrane (Millipore Corp., Waltham, Mass.).

The filtered, fetal rat liver extract (FRLE, 10–20 μl of a 1 mg/ml solution) was then applied to a pre-cast 20% native PHASTGEL® (50×40×0.45 mm, Pharmacia LKB Biotech AB, Upsala, Sweden) for separation by the PhastSystem gel electrophoresis (Pharmacia LKB Biotech AB, Upsala, Sweden). The electrophoretic conditions utilized were those suggested by the computer program of Olsson, I., et al., *Computer Program for Optimizing Electrophoretic Protein Separation*, 9 Electrophoresis 16 (1988). Following electrophoretic separation, $2 \times 10^4$ MEL cells were seeded onto the surface of the protein-containing PHASTGEL® and cultured for 7 days, thus allowing for differentiation and denucleation. After the 7 day incubation period, the PHASTGEL™/MEL cell culture was fixed in 0.4% paraformaldehyde in Phosphate-buffered saline (PBS) for approximately 2 hours, stained using a silver stain-based methodology, and the degree of differentiation and denucleation was determined using inverted-phase microscopy (Zeiss Axiophot Inverted Microscope, West Germany).

Figure 4A:
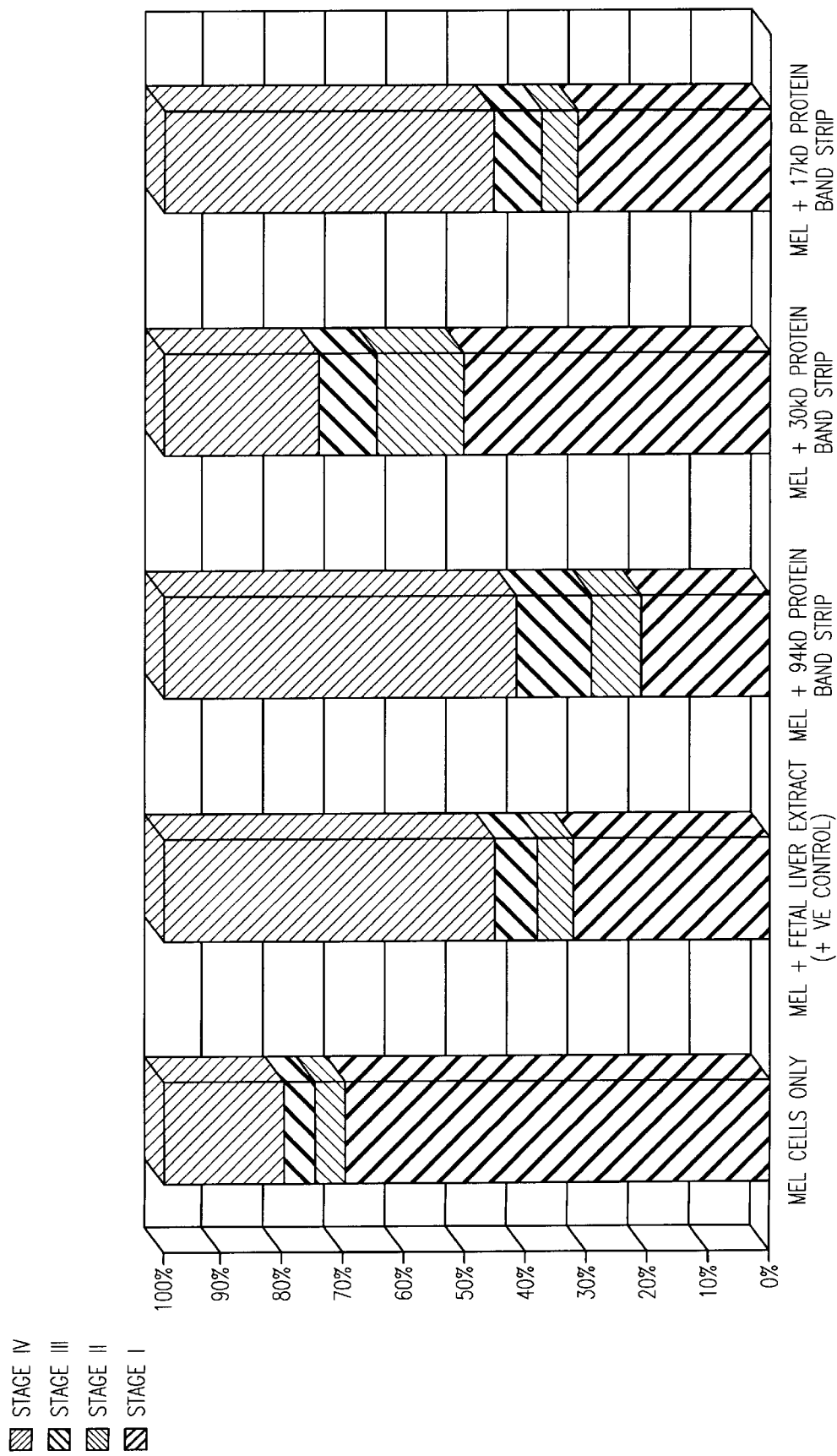

The results, as illustrated in FIG. 4A, demonstrated that at the PHASTGEL® regions which contained protein bands with apparent molecular weights of 17 kDa (EDDF1) and 94 kDa (EDDF2) there were increased numbers of differentiated and denucleated reticulocytes and mature red blood cells found to be present. In order to verify the presence of EDDF activities in these two bands, the PHASTGEL® was cut into 50 strips from top to bottom and each strip was co-cultured with MEL cells. The results, as illustrated in FIG. 4D, revealed that 60–70% of the MEL cells in the cultures containing the 17 kDa protein band (EDDF1) were differentiated and denucleated into reticulocytes and mature RBCs, as compared to 20% in the control cultures with no MAbs present. Similarly, FIG. 4C, revealed that 70% of the MEL cells in the cultures containing the 94 kDa protein band (EDDF2) were differentiated and denucleated into reticulocytes and mature RBCs. In contrast, FIG. 4B ~80% of the MEL cells in cultures with control gel strips (no EDDF) were found to be proerythroblasts and basophilic erythroblasts.

EXAMPLE 3

Production of Anti-EDDF Monoclonal Antibodies

In order to confirm the specific EDDF activity of the 17 kDa and 94 kDa proteins, the two bands were excised from the PHASTGEL® and the proteins contained therein were used as antigen in the immunization of BALB/c mice for subsequent preparation of anti-EDDF monoclonal antibodies (MAbs). The 17 kDa and 94 kDa protein bands were excised from a PhastSystem gel (1×30 mm gel containing 100 ng trophic factor) and utilized as antigens in the immunization of separate groups of Balb/c mice. Specifically, the EDDF-containing PHASTGEL® sections were excised and finely minced. The PHASTGEL® pieces were then mixed with an equal volume of complete Freund's adjuvant and directly injected intraperitoneally into the Balb/c mice. A total of 3 antigen immunizations were performed, with intraperitoneal injections of EDDF1-containing and EDDF2-containing PHASTGEL® in physiological saline on the 7th and 21st day following the initial immunization. The spleens of the Balb/c mice were harvested and allowed to fuse with either NS-1 or SP2/0 myeloma cells.

The resultant hybridomas were then screened utilizing MTT microassays and microscopic examination. From each hybridoma, two clones were selected as a function of their ability to inhibit, in MEL cell cultures, the differentiation and denucleation activities of EDDFs present in the extract and/or of the 17 kDa and 94 kDa proteins in the PHASTGEL® strips. The two MAbs specific for the 94 kD protein were designated MAb #15 and #59; whereas the 17 kDa MAbs were designated B7 or A12.

Figure 5:
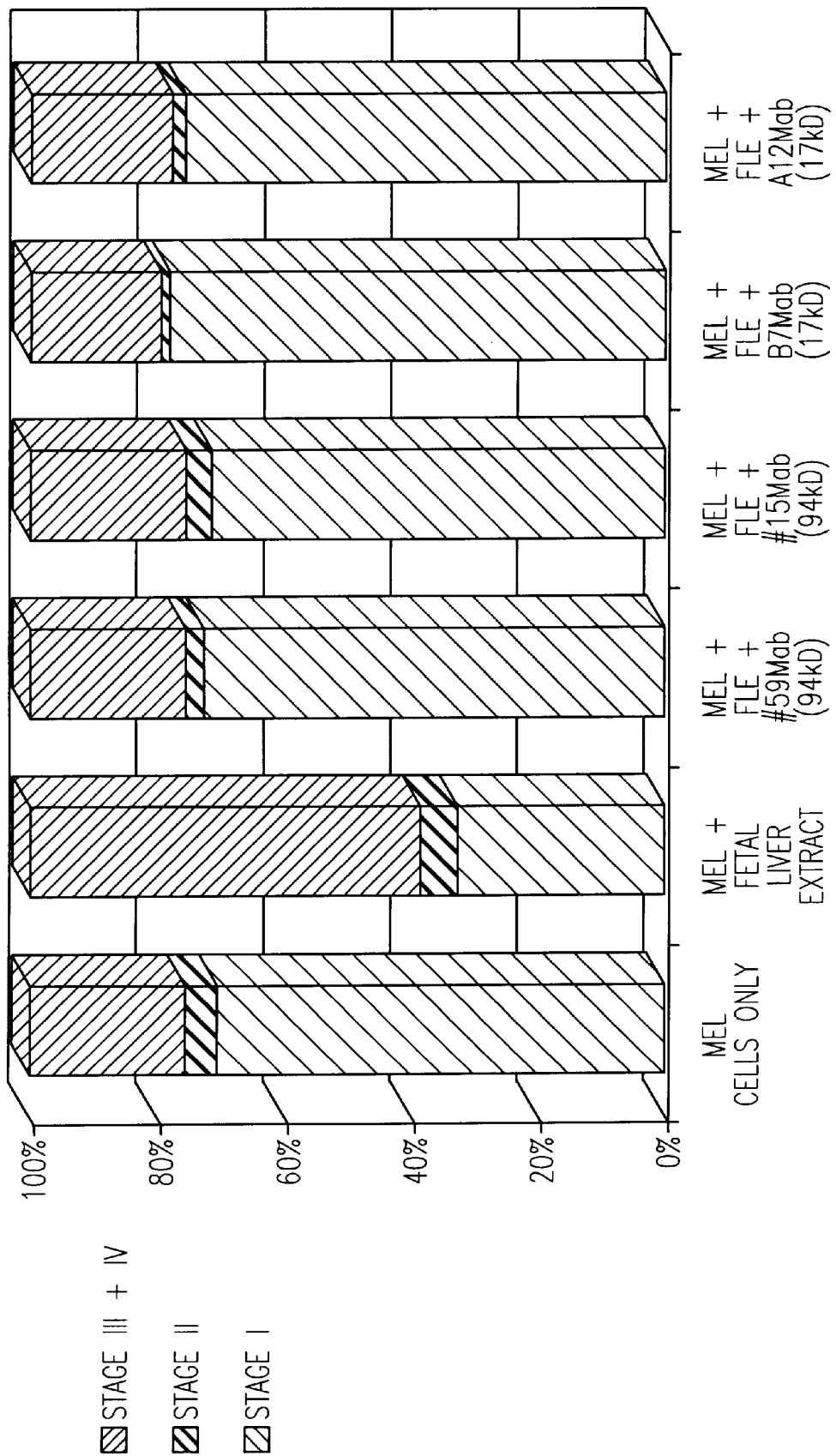
FIG. 5 Illustrates the inhibitory effect, as determined by a differential cell count, of selected monoclonal antibodies specific for fetal rat liver extract co-cultured with murine erythroid leukemia (MEL) cells.
Figure 6A:
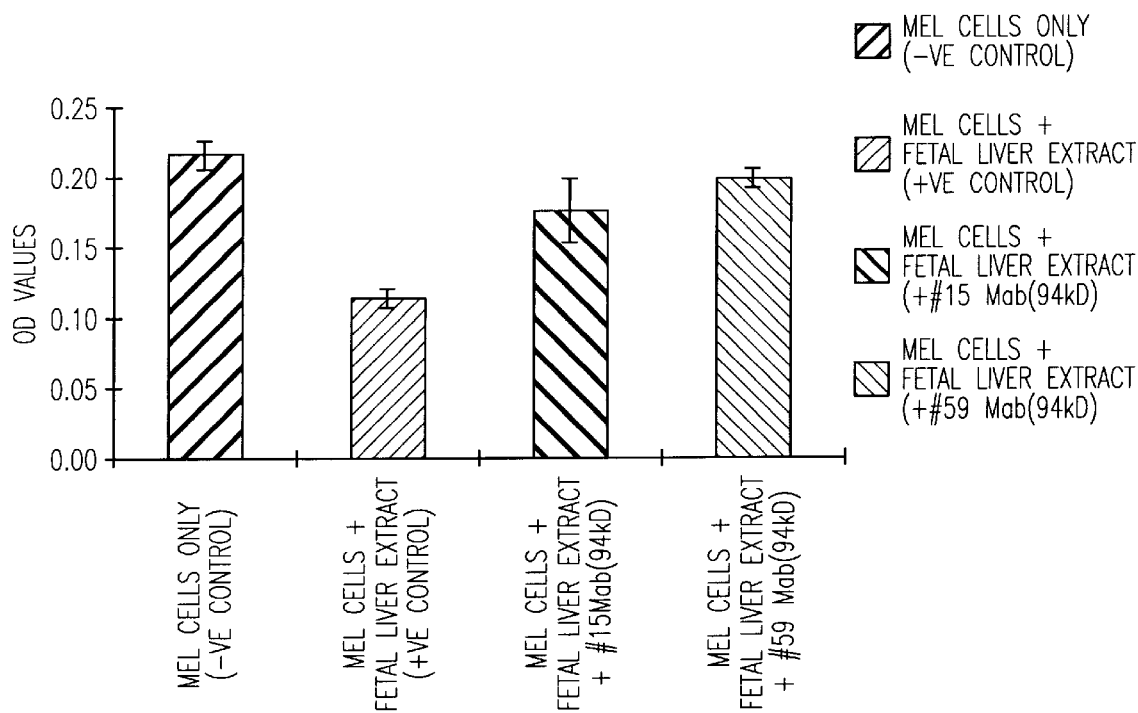
FIG. 6 FIG. 6A—Illustrates in histogram form the inhibitory effect, as determined by MTT microcolormetric assay, of the #15 and #59 monoclonal antibodies (specific for the 94 kD EDDF protein) directed against fetal liver extract on murine erythroid leukemia (MEL) cells. 6B—Illustrates in histogram form the inhibitory effect, as determined by MTT microcolormetric assay, of the B7 and A12 monoclonal antibodies (specific for the 17 kD EDDF protein) directed against fetal liver extract on murine erythroid leukemia (MEL) cells.
Figure 6B:
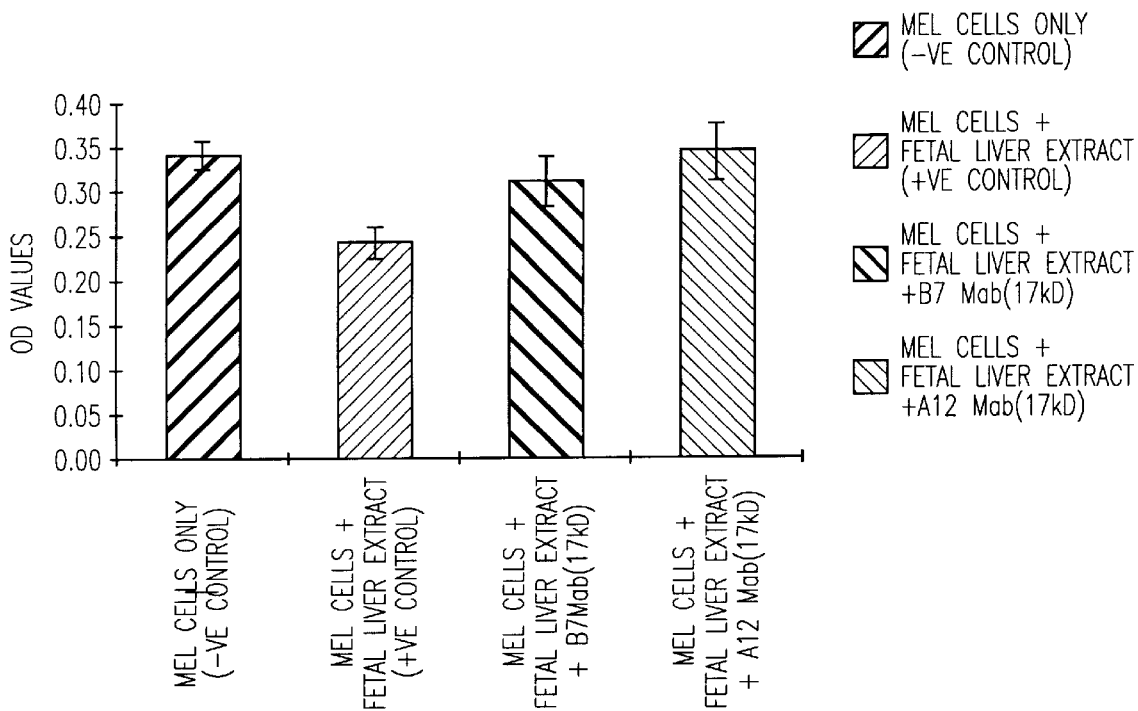

The results, illustrated in FIG. 5, demonstrated that approximately 70–74% of the MEL cells remained undifferentiated in the cultures with the EDDF and the specific MAb, as compared to ~20% in the control cultures with no MAb. FIG. 6A, panel a illustrates the results obtained by MTT microassay of cell culture O.D. of the MEL cells incubated with FRLE and the anti-94 kDa MAbs #15 and #59. Similarly, FIG. 6B, illustrates the results obtained by MTT microassay of cell culture O.D. of the MEL cells incubated with FRLE and the anti-17 kDa MAbs B7 and A12.

Figure 7:
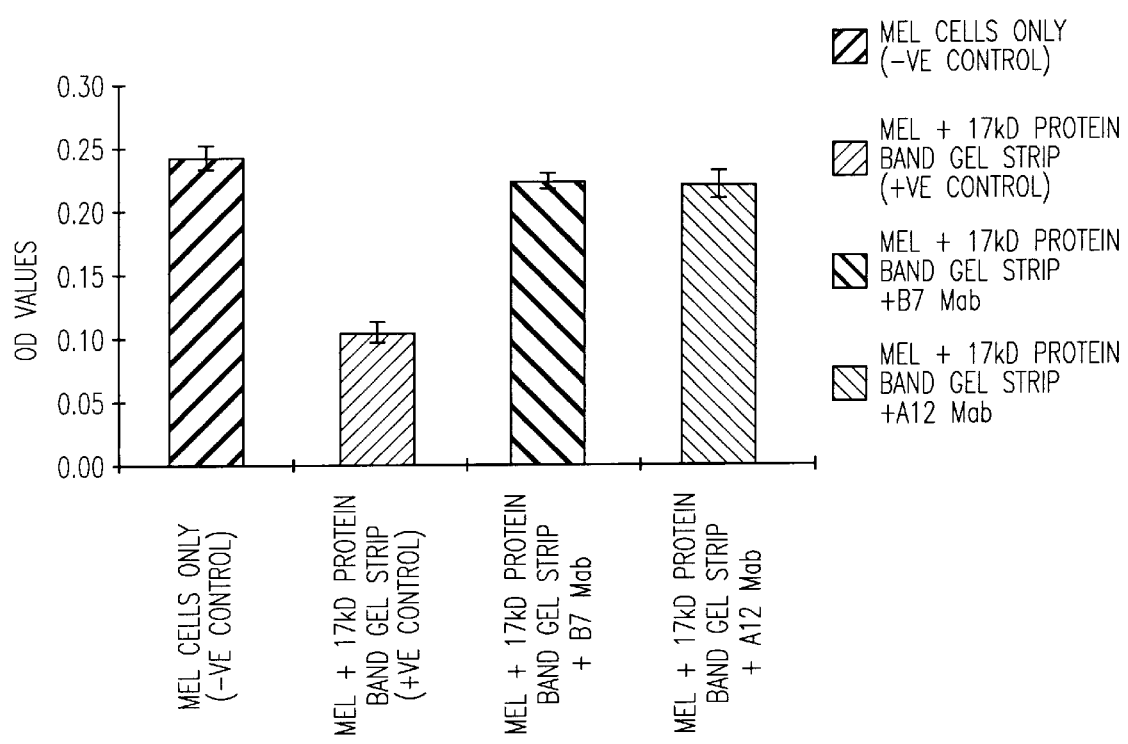
FIG. 7 Illustrates in histogram form the inhibitory effect, as determined by MTT microcolormetric assay, of monoclonal antibodies directed against individual PhastGel strips containing electrophoretically-separated fetal rat liver extract proteins co-cultured with murine erythroid leukemia (MEL) cells.

Additionally, an experiment was performed in which a PHASTGEL®, containing electrophoretically-separated FRLE proteins, was cut into 50 strips (1 mm/strip, with the orientation of the strip going from the top-to-bottom of the gel). The individual gel strips were co-cultured with $2 \times 10^4$ MEL cells with the two anti-17 kDa MAbs (B 7 and A12) in a 96-well culture plate for 7 days. The results of this assay are illustrated in histogram form in FIG. 7. These results suggested that clones had been selected which expressed fusion proteins with EDDF-like activities that possessed the ability to induce the differentiation and denucleation of 60% of the MEL cells. In addition, this aforementioned induction was inhibited by their specific "blocking" monoclonal antibodies.

EXAMPLE 4

Immunselection of Recombinant 17 kDa and 94 kDa Human EDDF Proteins

The selected EDDF-blocking monoclonal antibodies (EDDF-Mabs) were next utilized to immunoselect clones of human EDDF from a human bone marrow cDNA library (produced by Clonetech Co., Palo Alto, Calif.). The immunoscreening procedure utilized was a modification of that described in Young, R. A., and Davis, R. W., *Efficient Isolation of Genes Using Antibody Probes*, 80 Proc. Nat'l Acad. Sci USA 1194 (1983), whose disclosure is incorporated herein by reference. The aforementioned modification consisted of using ammonium nickel sulfate as an enhancing agent to increase 100-fold the sensitivity of the peroxidase-avidin-biotin complex reaction utilizing diamino-benzidine as the substrate. A maximum of 4 nitrocellulose membrane "replicas" were made from each colony plate for immunoscreening and only the most intensely-stained clones were selected in the immunoscreening procedure. The selected clones were then allowed to express the recombinant proteins which were subsequently assayed to determine their potential EDDF-specific biological activity in vitro. It should be noted that only the clones with the highest EDDF-specific biological activity in the MEL cell cultures were selected for further analysis.

A total of four EDDF-specific monoclonal antibodies were selected. The two MAbs specific for the 94 kDa protein (#15 and #59) and the two 17 kDa-specific MAbs (B7 and A12) were utilized as immunoprobes in the screening of positive expression clones from a selected human bone marrow cDNA library. In brief, the precipitation procedure for the cDNA library involved the isolation of mRNAs from cells of the human bone marrow library, followed by reverse transcription to synthesize the EDDF cDNAs. The selected, EDDF-specific cDNAs were ligated into a gt-11 phage vector and subsequently transformed in an *E. coli* strain Y1090 host bacteria. The cDNA insert of the gt-11 clone would then be sub-cloned into an in vitro expression vector system for protein expression.

(a) Preparation and Purification of 17 kD EDDF1/gt-11 Phage

A cDNA was synthesized from a 17 kDa EDDF1 mRNA selected from the human bone marrow library. The EDDF1 cDNA was ligated into a gt-11 phage and the resulting recombinant gt-11 clone was designated Lambda.17 kDa.EDDF1 (or EDDF1-A12).

Purified Lambda.17 kDa.EDDF1 was obtained by the following methodology: 10 plaque-forming units (pfu) of EDDF/gt-11 phage was inoculated into a 500 ml overnight culture of *E. coli* stain Y1090 until complete lysis of the bacteria was observed. The Lambda phage were recovered and purified by centrifugation and enzymatic treatment with RNase and DNase in an NaCl/PEG 8000 solution, followed by high speed CsCl density gradient centrifugation to collect the purified phage at a final gradient density of approximately 1.5 gm CsCl/ml.

Isolation and purification of the Lambda.17 kDa.EDDF1 DNA was facilitated by initial digestion of the Lambda phage (1 ml) in EDTA, SDS, and proteinase K, followed by repeated extractions with phenol, phenol/chloroform, and chloroform. The EDDP1 DNA was then ethanol precipitated with 95% ethanol and collected by centrifugation. Following repeated washes in 70% ethanol, the resultant Lambda.17 kDa.EDDF1 DNA pellet was redissolved in Tris-EDTA buffer.

(b) Recovery of the 17 kDa EDDF1 cDNA Insert from Lambda.17 kDa.EDDF1

10 g of Lambda.17 kDa.EDDF1 DNA was digested overnight with EcoRl and electrophoresed. The results of the EcoRl digestion demonstrated the presence of three discreet DNA fragments: (1) 0.65 kbp fragment designated as the EDDF1; (2) a 2.06 kbp fragment designated as the large DNA fragment; and (3) a 46 kbp fragment designated as the Lambda phage DNA. Three discreet DNA fragments were observed due to the presence of an internal EcoRl restriction site within the Lambda.17 kDa.EDDF1 cDNA insert located at the position of base pair 2066.

Following electrophoresis, the 0.65 kbp EDDF1 DNA fragment was visualized utilizing U.V. light, excised from the agarose gel, and recovered via standard techniques. The recovered EDDF1 cDNA was then prepared for High Protein Expression by recombination with the pGEX-1 Lambda T EcoRl/BAP vector.

EXAMPLE 5

DNA Sequencing of Lambda.17 kDa.EDDF1

Lambda.17 kDa.EDDF1 was sequenced utilizing 5' and 3' Lambda phage sequencing primers and TAQ® polymerase (Pharmacia Biotech) in an automated DNA sequencing apparatus (ABI). This sequencing methodology provided extremely accurate and reproducible results with respect to the DNA sequencing of the Lambda phage "hosting" the EcoRl-generated fragments. The DNA sequencing indicated that the large EDDF1 fragment consisted of 2721 bp, SEQ ID NO:1 whereas the smaller DNA fragment was found to consist of 656 bp, SEQ ID NO:2. Moreover, only 288 bp, SEQ ID NO:3 of the aforementioned 656 bp, SEQ ID NO:2 sequence was subsequently shown (by computer-based intron/exon analysis) to be translated into the human, recombinant EDDF1 (hrEDDF1) protein.

Figures 8B, 8C, 9:
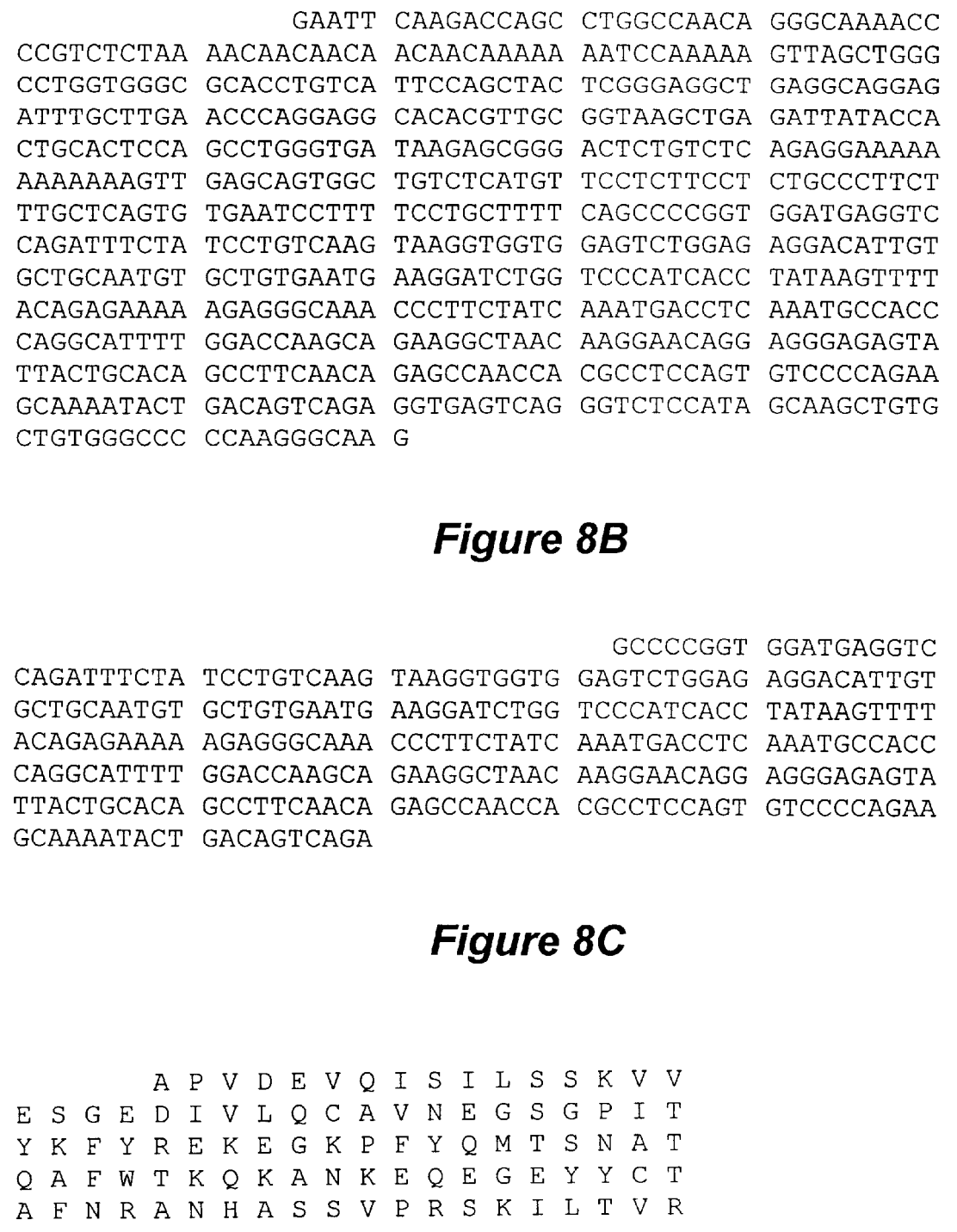

FIG. 8A depicts the DNA sequence of the large, 2721 bp EDDF1 EcoRl-generated cDNA, SEQ ID NO:1 fragment derived from the human bone marrow cDNA library. FIG. 8B depicts the DNA sequence of the smaller, 656 bp EcoRl-generated cDNA fragment, SEQ ID NO:2. FIG. 8C depicts the DNA sequence of the 288 bp EcoRl-generated, translatable hrEDDF1, SEQ ID NO:3. By standard convention the DNA sequence is shown in the 5' to 3' orientation.

EXAMPLE 6

Sub-Cloning of the 17 kDa EDDF1 EcoRl-Generated Fragments

The EcoRl-generated, 288 bp EDDF1 DNA fragment (see FIG. 8C and SEQ ID NO. 3) was sub-cloned into the pGEX-1 Lambda T EcoRl/BAP High Protein Expression vector (hereinafter pGEX). The pGEX vector was selected due to the following factors: (1) it possessed a high efficiency transcriptional promotor at its 5'-terminus and a 3'-terminus poly(A) tail; and (2) it provided an easy methodology for the purification of the two EDDF recombinant proteins via affinity column chromatography-based purification of the glutathione-S-transferase (GST)-containing EDDF1 fusion proteins.

a. Transformation of Recombinant Plasmid

The pGEX vector was digested with EcoRl. The digested pGEX vector was then incubated overnight with the EcoRl-generated, 288 bp EDDF1 DNA fragments (hereinafter EDDF1-288, SEQ ID NO:3) in the presence of T4 DNA ligase. Following ligation, competent *E. coli* strain DH5 bacteria were transformed with the recombinant vector and transferred onto Luria broth (LB) agar plates containing 100 g/ml ampicillin for overnight incubation. Due to the fact that the pGEX vector contained a gene which conferred ampicillin resistance to the transformed bacteria, the use of ampicillin screening allowed the exclusive selection of transformed bacterial colonies, as only those bacteria containing the recombinant vector would be viable in its presence.

b. Identification and Isolation of the EDDF1-288 Transformants

The transformed bacterial colonies were individually selected, inoculated into a small volume of LB medium containing 100 g/ml ampicillin, and incubated for approximately 3 hours. Following incubation, the transformed bacteria were collected via centrifuigation for subsequent isolation of the recombinant vector DNA by the alkaline lysis "mini prep" technique as described in Maniatis, T., Fritsch, E. F., and Sambrook, J., *Molecular Cloning, 2nd ed.*, Cold Spring Harbor Laboratory, Cold Spring Harbor, N.Y. pp. 134–136 (1986). With this technique, the collected bacteria were lysed by the addition of a Tris-EDTA/NaOH/SDS solution with vigorous vortexing. After centrifugation to collect contaminating cellular debris, the recombinant vector DNA-containing supernatant was aspirated, extracted with phenol and chloroform, and precipitated with 95% ethanol. The mixture was centrifuged to collect the precipitated DNA and the nucleic acid pellet was dissolved in Tris-EDTA buffer.

The collected recombinant vector DNA was then digested with EcoRl to release the EDDF1-288, SEQ ID NO:3 insert from the 4.9 Kbp pGEX vector. The digested DNA was subjected to agarose gel electrophoresis and the individual DNA bands were identified via U.V. light visualization.

"Positive" bacterial colonies (i.e., those which contained the EDDF1-288, SEQ ID NO:3 insert) were selected and inoculated into LB medium for large scale plasmid purification via alkaline lysis and PEG precipitation. The purified recombinant vector DNA was then transfected into an *E. coli* strain BL-21 host bacterium to facilitate high levels of expression of human recombinant EDDF1-288 (hrEDDF1-288) protein, SEQ ID NO:4.

EXAMPLE 7

Expression and Amplification of Recombinant Human EDDF Proteins

The pGEX-EDDF1-288 recombinant molecule was transfected into *E. coil* stain BL-21 competent bacteria in 50 ml of LB medium. IPTG was utilized to induce high levels of expression of the human recombinant EDDF1-228 (hrEDDF1-288) protein, SEQ ID NO:4. Collected bacteria were lysed, frozen, and thawed a total of 4-times using liquid nitrogen, sonicated, and centrifuged. The supernatant, containing the hrEDDF1-288 fusion protein, SEQ ID NO:4 was then passed through an anti-GST affinity chromatography column containing anti-GST monoclonal antibodies (Pharmacia). The use of this type of affinity chromatography allowed purification of the GST-hrEDDF1-288 fusion protein which was bound to the matrix through the GST moiety. Following a high salt wash, the GST-hrEDDF1-288 fusion protein was eluted. The proteolytic enzyme thrombin was utilized to cleave the linkage between the hrEDDF1-288 protein, SEQ ID NO:4 and the GST moiety and the purified hrEDDF1-288 protein, SEQ ID NO:4 was collected for subsequent in vivo and in vitro assays.

EXAMPLE 8

Determination of In Vitro Biological Activity of the hrEDDF1-288 Protein

The MEL cell line was utilized to determine the biological activity (i.e., the differentiation and denucleation activity) of the hrEDDF1-288 protein in vitro. The MEL cells were co-cultured with the hrEDDF1-288 protein, SEQ ID NO:4 for 3 days in DMEM medium supplemented with 15% FCS. After 3 days of co-culture, an MTT microassay was performed to determine the degree of inhibition of MEL cell proliferation by the hrEDDF1-288 protein, SEQ ID NO:4. After 6 days of co-culture, a differential cell count assay was performed to determine the degree of differentiation and denucleation of the MEL cells into mature erythrocytes.

EXAMPLE 9

Amino Acid Sequence of the hrEDDF1-288 Protein

FIG. 9 depicts the amino acid sequence of the hrEDDF1-288 protein, SEQ ID NO:4 translated from the 288 bp hrEDDF1-288 DNA fragment, SEQ ID NO:3. Subsequent analysis following both nucleic acid and amino acid sequencing indicated that hrEDDF1-288 protein, SEQ ID NO:4 possessed almost complete homology with human platelet-endothelial cell adhesion molecule-1 (PECAM-1). Specifically, the hrEDDF1-288 protein, SEQ ID NO:4 was homologous to that which was found in exon 8 of the PECAM-1 molecule. See Newman, P. J., U.S. Pat. No. 5,264,554; Newman, P. J. et al., PCT Publication WO 96/01271. Although there is sequence homology between these two molecules, the in vivo and in vitro biological functions are completely diverse in that EDDF1 functions in the differentiation and denucleation of erythrocytes and PECAM-1 is involved in cellular adhesion processes.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein. The invention, therefore, is not to be restricted in any manner except in the spirit of the appended claims.

What is claimed is:

1. A method of differentiating erythrocyte progenitor cells comprising administering to the erythrocyte progenitor cells an effective amount of a purified polypeptide having a sequence according to SEQ ID NO:4, such that the erythrocyte progenitor cells differentiate.

2. The method of claim 1, where the effective amount of a purified polypeptide having a sequence according to SEQ ID NO:4 causes the erythrocyte progenitor cells to differentiate into reticulocytes.

3. The method of claim 1, where the effective amount of a purified polypeptide having a sequence according to SEQ ID NO:4 causes the erythrocyte progenitor cells to differentiate into mature erythrocytes.

4. A method of causing denucleation of erythrocyte progenitor cells comprising administering to the erythrocyte progenitor cells an effective amount of a purified polypeptide having a sequence according to SEQ ID NO:4, such that the erythrocyte progenitor cells denucleate.

* * * * *